United States Patent [19]

Satzinger et al.

[11] Patent Number: 4,563,471

[45] Date of Patent: Jan. 7, 1986

[54] 4-OXOTHIAZOLIDIN-2-YLIDENE-ACETAMIDE DERIVATIVES AS CNS AGENTS

[75] Inventors: Gerhard Satzinger, Denzlingen; Manfred Herrmann; Edgar Fritschi, both of St. Peter; Johannes Hartenstein, Stegen-Wittental; Gerd Bartoszyk, Waldkirch, all of Fed. Rep. of Germany

[73] Assignee: Warner-Lambert Company, Morris Plains, N.J.

[21] Appl. No.: 608,298

[22] Filed: May 8, 1984

[30] Foreign Application Priority Data

May 10, 1983 [DE] Fed. Rep. of Germany ....... 3317000

[51] Int. Cl.$^4$ ................ C07D 277/34; A61K 31/425
[52] U.S. Cl. ..................................... 514/369; 548/187
[58] Field of Search ........................ 548/187; 514/369

[56] References Cited

U.S. PATENT DOCUMENTS 4,018,775  4/1977  Satzinger ..................... 260/293.68

*Primary Examiner*—Robert Gerstl
*Attorney, Agent, or Firm*—Ronald A. Daignault

[57] ABSTRACT

4-Oxothiazolidin-2-ylidene-acetamide derivatives, processes for their preparation, pharmaceutical compositions and a method for treating diseases of the central nervous system such as epilepsy are described.

7 Claims, No Drawings

4-OXOTHIAZOLIDIN-2-YLIDENE-ACETAMIDE DERIVATIVES AS CNS AGENTS

SUMMARY OF INVENTION

The invention concerns 4-oxothiazolidin-2-ylidene-acetamide derivatives of the general formula I

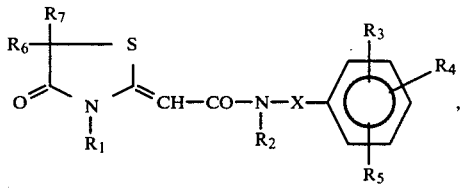

in which $R_1$ signifies a hydrogen atom, a saturated or unsaturated, straight-chained or branched aliphatic hydrocarbon radical with up to four carbon atoms, an aryl or aralkyl group, $R_2$ signifies a hydrogen atom or a straight-chained or branched alkyl- or dialkylaminoalkyl radical with up to nine carbon atoms, X signifies a valency bond or a straight-chained or branched alkylene chain with up to four carbon atoms and the radicals $R_3$, $R_4$, and $R_5$, which can be the same or different, signify a hydrogen atom, a straight-chained or branched alkyl radical with up to four carbon atoms, a straight-chained or branched alkoxy or alkylthio group with up to four carbon atoms, whereby two neighboring radicals can together also form a methylenedioxy or ethylenedioxy group, a halogen atom, a hydroxy group, a nitro group, a carboxyl group or a lower alkoxycarbonyl radical with up to five carbon atoms and $R_6$ and $R_7$ which can be the same or different signify a hydrogen atom or a straight-chained or branched alkyl radical containing up to four carbon atoms, or a pharmaceutically acceptable acid addition salt thereof.

The compounds I are prepared by means of analogous processes and used in the treatment of diseases related to the central nervous system, especially of epilepsy.

DETAILED DESCRIPTION

The invention concerns new 4-oxothiazolidin-2-ylidene-acetamide derivatives of the general formula

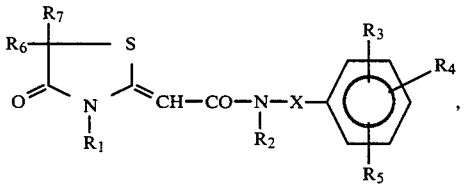

in which $R_1$ signifies a hydrogen atom, a saturated or unsaturated, straight-chained or branched aliphatic hydrocarbon radical with up to four carbon atoms, an aryl or aralkyl group, $R_2$ signifies a hydrogen atom or a straight-chained or branched alkyl- or dialkylaminoalkyl radical with up to nine carbon atoms, X signifies a valency bond or a straight-chained or branched alkylene chain with up to 4 carbon atoms and residues $R_3$, $R_4$, and $R_5$, which can be the same or different, signify a hydrogen atom, a straight-chained or branched alkyl radical with up to 4 carbon atoms, a straight-chained or branched alkoxy or alkylthio group with up to four carbon atoms, whereby two neighboring radical can together also from a methylenedioxy or an ethylenedioxy group, a halogen atom, a hydroxy group, a nitro group, a carboxyl group or a lower alkoxycarbonyl radical with up to five carbon atoms and $R_6$ and $R_7$ which can be the same or different signify a hydrogen atom or a straight-chained or branched alkyl radical containing up to four carbon atoms or a pharmaceutically acid addition salt thereof.

A saturated or unsaturated, straight-chained or branched aliphatic hydrocarbon radical with up to four carbon atoms includes an alkyl radical of from one to four carbon atoms such as methyl, ethyl, n-propyl, isopropyl, n-butyl, sec-butyl, isobutyl or tertiary-butyl, and an alkenyl radical from two to four carbon atoms such as vinyl, allyl, 1-butenyl, cis or trans-2-butenyl, 2-methyl-1-propenyl and 3-methyl-1-propenyl.

An aryl group is an aromatic hydrocarbon such as phenyl or naphthyl and the like. Preferably, aryl is phenyl or phenyl substituted by alkyl or from one to four carbon atoms, alkoxy of from one to four carbon atoms, halogen or trifluoromethyl.

An aralkyl group is an aryl group as defined above attached to an alkyl chain of one to four carbon atoms such as, for example, benzyl, α-methylbenzyl, phenethyl and the like.

As examples of straight-chained or branched alkyl- or dialkyl-aminoalkyl radicals with up to a total of nine carbon atoms, there are methylaminomethyl, dimethylaminomethyl, ethylaminomethyl, diethylaminomethyl, propyl- or isopropylaminomethyl, N-ethyl-N-methylaminomethyl, N-propyl-N-methylaminomethyl, N-isopropylaminomethyl, N-isopropyl-N-ethylaminomethyl, dimethylaminoethyl, methylaminoethyl, diethylaminoethyl, di-isopropylaminoethyl, N-ethyl-N-propylaminoethyl, methylaminopropyl, dimethylaminopropyl, diethylaminopropyl, di-isopropylaminopropyl, N-methyl-N-ethylaminopropyl and the like.

Halogen atoms are those of the known periodic group of elements and preferably include fluorine, chlorine or bromine.

When $R_2$ is signified by a straight or branched alkyl- or dialkylaminoalkyl radical as defined above, the resulting compounds of formula I are bases and may thus be converted by known means into suitable pharmaceutically acceptable acid addition salts. As such, they include salts or organic and inorganic acids such as, for example, hydrochloric, hydrobromic, sulfuric, phosphoric, acetic, maleic, fumaric, oxalic and succinic acids.

Compounds of the general formula I are preferred in which $R_1$ signifies a hydrogen atom, a saturated or unsaturated alkyl radical with one to three carbon atoms, a phenyl or benzyl radical, $R_2$ signifies a hydrogen atom, a methyl or ethyl group or a dialkylaminoalkyl radical with up to seven carbon atoms, X signifies a valency bond or a straight-chained or branched alkylene group with one to three atoms and $R_3$, $R_4$, and $R_5$, which can be the same or different, signify a hydrogen atom, a methyl, ethyl, methoxy, ethoxy, methylthio or ethylthio group, whereby two neighboring radicals can together also form a methylenedioxy group, a fluorine, chlorine, bromine, iodine atom or a hydroxy group or a nitro group or a carboxyl radical or a lower alkoxycarbonyl radical with up to five carbon atoms and $R_6$ and $R_7$ which can be the same or different signify a hydrogen atom or a methyl or ethyl group.

Especially preferred are compounds of the general formula I, in which $R_1$ signifies a hydrogen atom, a methyl, ethyl, allyl or benzyl radical, $R_2$ signifies a hydrogen atom, a methyl radical, a valency bond or an ethylidene group and $R_3$, $R_4$ and $R_5$, which can be the same or different, signify a hydrogen atom, a methyl radical or a chlorine or bromine atom and $R_6$ and $R_7$ signify a hydrogen atom.

A further subject of the invention is a process for the preparation of compounds of the general formula I, characterized in that one either (a) reacts a compound of the general formula II

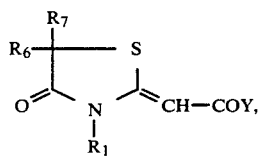

in which $R_1$, $R_6$ and $R_7$ have the above-mentioned meaning and Y represents a reactive group, in per se known manner with a compound of the general formula III

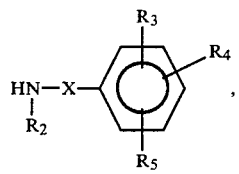

in which the residues $R_2$, $R_3$, $R_4$ and $R_5$ and X have the above-mentioned meaning, and possibly subsequently N-alkylates or (b) reacts a compound of the general formula IV

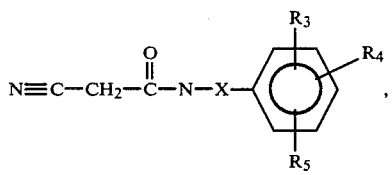

in which the residues $R_3$, $R_4$ and $R_5$, as well as X, have the above-mentioned meaning, with a thioglycolic acid ester of the general formula V

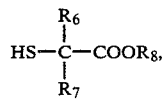

in which $R_6$ and $R_7$ have the above-mentioned meaning and $R_8$ represents a lower alkyl radical with up to five carbon atoms, if desired, subsequently N-alkylates in per se known manner the compound obtained of the general formula VI

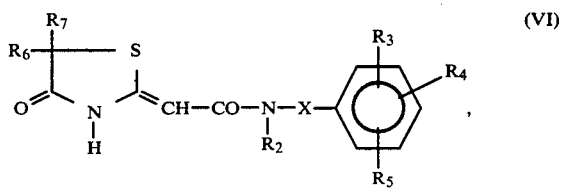

in which $R_2$, $R_3$, $R_4$, $R_5$, $R_6$ and $R_7$, as well as X, have the above-mentioned meaning, and isolates the so obtained compounds of the general formula I in per se known manner.

The compounds of the general formula I are valuable medicaments with unusually wide anti-convulsive activity profile and outstanding compatibility. They are especially suitable for a comprehensive antiepileptic therapy.

The term epilepsy is a collective designation for a class of chronic diseases of the central nervous system which have in common the appearance of episodic attacks with abnormal motor ("cramps"), sensory and psychic penomena.

The frequency of epilepsies is surprisingly large and lies at about 0.5% of the population. The extensiveness of forms of the epilepsies obliges a pharmacotherapy which, due to the necessity of a frequently changing, differentiated treatment with different pharmaceuticals, is very complicated.

Antiepileptic substances belong to the most varied chemical classes. These include barbiturates, pyrimidones, hydantoins, oxazolidinediones, succinimides, benzodiazepines, iminostilbenes and valproates. Corresponding to their actions in laboratory models, representatives of these classes are more or less suitable for the therapy of partial (focal), generalized, temporal or myoclonic attacks and absences. Consequently, an ideal antiepileptic would be a substance which is able to suppress all kinds of attacks and absences and produces no undesired side effects.

A disadvantage of the known antiepileptics is that, in the case of the attempt to control attacks, they often fail and, furthermore, can cause CNS functional disturbances and other side effects going as far as aplastic anaemia (Goodman, Gilman, The Pharmacological Basis of Therapeutics, 6th ed., 1980, p. 451 et seq.). Even when one employs known anti-convulsives in suitable selection and combination, in the case of only 50% of the treated patients can occurring attacks be brought under control. However, even in successful cases, as a rule unpleasant side effects must be put up with.

However, the compounds of the general formula I are characterized not only by an extraordinary breadth of their activity spectrum but also by a high potency and an extremely good compatibility. Although these findings can first only be supported by animal experiments, it is to be expected that the compounds of the invention signify a considerable advance in the case of the treatment of epilepsy in their multitudinous forms of manifestation.

The compounds of the general formula I can, on the basis of the C—C double bond on the thiazolidine ring, occur in a Z- or E-configuration. The present invention includes both forms.

The starting compounds II and III are known or can be prepared according to known methods. Compounds of the general formula II, in which $R_1$ is a hydrogen atom, can be obtained starting from the known acids (R₁=H, Y=OH) by alkylation on the ring nitrogen after previous esterification by means of lower aliphatic alcohols and subsequent careful hydrolysis (Annalen, 665 (1963), p. 150 et seq.).

In especially advantageous manner, the corresponding t-butyl esters (Y=tert.-butoxy group) are thereby used.

The process (a) is preferably carried out in an aprotic bipolar solvent, such as e.g. dichloromethane, Chloroform or dimethylformamide, or in mixtures of such solvents.

As reactive groups, there come into question e.g. anhydrides, alkyl esters, mixed anhydrides but especially the halides.

However, the reaction can also be carried out with the use of alkyl esters (Y=lower alkoxy group).

The especially reactive acid chlorides are prepared in that one reacts the free acid (Y=OH) with a suitable acid halide, such as e.g. thionyl chloride, oxalyl chloride or phosphorus pentachloride.

The compounds of the general formula IV can be prepared—starting from cyanoacetic acid esters—such as e.g. cyanoacetic acid ethyl ester, with corresponding aniline derivatives of the general formula VII

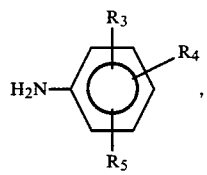

(VII)

in which R₃, R₄ and R₅ have the above-mentioned meaning, according to generally known processes, e.g. by heating of the reaction components with distilling off of the liberated ester alcohol.

The compounds of general formula I, in which R₁ signifies a hydrogen atom, are preferably prepared according to process (b) since process (a) gives, in individual cases, unsatisfactory yields.

The compounds I according to the invention can be administered enterally or parenterally as pharmaceutical compositions in liquid or solid form. As injection medium, there are used especially aqueous phases which contain the usual additives, such as stabilizing agents and solubilizing agents. Solid carrier materials are e.g. starch, lactose, mannitol, methyl cellulose, talc, highly dispersed silicic acids, high molecular fatty acids (such as stearic acid), gelatine, agar-agar, calcium phosphate, magnesium stearage, animal and vegetable fats, solid high molecular polymers (such as polyethylene glycols); compositions suitable for oral administration can, if desired, contain flavoring and/or sweetening materials.

The dosage of the compounds according to the invention depends upon the nature and severity of the particular disease. The oral individual dosage amounts to about 10–200 mg.

The following Examples serve for the more detailed explanation of the invention:

EXAMPLE 1

(Z)-4-(Oxothiazolidin-2-ylidene)-N-(2,6-dimethylphenyl)-acetamide.

4.2 g (35 mmole) thioglycolic acid ethyl ester are mixed with 6.6 g (35 mmole) cyanoacetic acid 2,6-dimethylanilide and 0.13 g (1 mmole) potassium carbonate.

Subsequently, 15 ml ethanol are added thereto and the mixture is heated to the boil for 3.5 hours, with stirring. One then adds a further 15 ml ethanol thereto and cools to 40° C. The precipitated deposit is filtered off with suction, the crude product is recrystallized from 50% aqueous acetic acid, washed neutral with water and dried in a vacuum. One obtains (Z)-(4-oxothiazolidin-2-ylidene)-N-(2,6-dimethylphenyl)-acetamide; m.p. 250° C. (decomp.).

The cyanoacetic acid 2,6-dimethylanilide used as starting product is prepared as follows:

11.3 g (0.1 mole) cyanoacetic acid ethyl ester and 15.7 g (0.13 mole) 2,6-dimethylaniline are mixed and heated to 170° C., with stirring. The resulting ethanol is thereby continuously distilled off; the temperature hereby increases to 195° C. After six hours, the reaction is ended.

After cooling, the flask content is recrystallized from 350 ml ethanol. One obtains the cyanoacetic acid 2,6-dimethylanilide in the form of colorless crystals of the mp 204°–206° C.

EXAMPLE 2

(Z)-(3-Methyl-4-oxothiazolidin-2-ylidene)-N-(2,6-dimethylphenyl)-acetamide

Variant A 0.1 Mole (Z)-3-methyl-4-oxothiazolidin-2-ylidene)-acetic acid are dissolved in a mixture of 500 ml dichloromethane and 5 ml dimethylformamide and 10 ml thionyl chloride, dissolved in 30 ml dichloromethane, are added dropwise thereto within 45 minutes at room temperature. One allows the reaction mixture to stir further for 15 minutes at this temperature and evaporates the now brown solution in a vacuum. The residue is dissolved in 500 ml dichloromethane. Into the filtered solution one then adds dropwise, within 30 minutes, a solution of 0.2 mole 2,6-dimethylaniline in 30 ml dichloromethane at room temperature and further stirs for four hours at 40° C.

The precipitated deposit is filtered off with suction and recrystallized from 50% aqueous acetic acid, washed neutral with water and dried in a vacuum.

One obtains (Z)-(3-methyl-4-oxothiazolidin-2-ylidene)-N-(2,6-dimethylphenyl)-acetamide. Mp 250.4° C. (decomp.).

The (Z)-(3-methyl-4-oxothiazolidin-2-ylidene)-acetic acid used as starting product is prepared as follows:

20 g (Z)-(3-methyl-4-oxothiazolidin-2-ylidene)-acetic acid t-butyl ester (Annalen, 665 (1963), p. 150 et seq.) are dissolved in 45 ml glacial acetic acid and mixed at 0° C. with 8 ml of a 33% solution of hydrobromic acid in glacial acetic acid. After 15 minutes, it is mixed with ice water and the precipitated acid is filtered off with suction. Since the end product decomposes rapidly, it is quickly recrystallized from isopropanol. The free acid obtained can be further used directly.

Variant B 0.020 Mole (Z)-(4-oxothiazolidine-2-ylidene)-N-(2,6-dimethylphenyl)-acetamide are mixed dropwise at room temperature in 22 ml 1N sodium hydroxide solution with 2.3 g (0.024 mole) dimethyl sulphate and allowed to stir for a total of one hour. Thereafter, one extracts the methylation product with dichloromethane and obtains, after usual working up and crystallization from methanol, (Z)-(3-methyl-4-oxothiazolidin-2-ylidene)-N-(2,6-dimethylphenyl)-acetamide of the mp 250.4° C. (decomp.).

One obtains the following compounds in a manner analogous to that described in Example 2:

- (b) (Z)-(3-methyl-4-oxothiazolidin-2-ylidene)-N-(2-chlorophenyl)-acetamide; mp 193°–194° C. (decomp.) (methanol)
- (c) (Z)-(3-methyl-4-oxothiazolidin-2-ylidene)-N-(3-chlorophenyl)-acetamide; mp 275.3° C. (decomp.) (dimethyl sulphoxide=DMSO)
- (d) (Z)-(3-methyl-4-oxothiazolidin-2-ylidene)-N-(4-chlorophenyl)-acetamide; mp 295.5° C. (decomp.) (DMSO-methanol)
- (e) (Z)-(3-methyl-4-oxothiazolidin-2-ylidene)-N-(2,3-dimethylphenyl)-acetamide; mp 205°–207° C. (decomp.) (ethanol)
- (f) ($\pm$)-(Z)-(3-methyl-4-oxothiazolidin-2-ylidene)-N-(1-phenylethyl)-acetamide; mp 122°–125° C. (propan-2-ol/petroleum ether)
- (g) (−)-(Z)-(3-methyl-4-oxothiazolidin-2-ylidene)-N-(1-phenylethyl)-acetamide; mp 55°–60° C. (dichloromethane)
- (h) (+)-(Z)-(3-methyl-4-oxothiazolidin-2-ylidene)-N-(1-phenylethyl)-acetamide; mp 65°–70° C. (dichloromethane)
- (i) (Z)-(3-methyl-4-oxothiazolidin-2-ylidene)-N-(2-chloro-6-methylphenyl)-acetamide; mp 244°–245° C. (ethanol)
- (j) (Z)-(3-methyl-4-oxothiazolidin-2-ylidene)-N-(2,6-dichlorophenyl)-acetamide; mp 224°–226° C. (toluene)
- (k) (Z)-(3-methyl-4-oxothiazolidin-2-ylidene)-N-(1,2,4,6-trimethylphenyl)-acetamide; mp 249.8° C. (decomp.) ethanol)
- (l) (Z)-(3-methyl-4-oxothiazolidin-2-ylidene)-N-bromo-2,6-dimethylphenyl)-acetamide; mp 263° C. (methanol)
- (m) (Z)-(3-methyl-4-oxothiazolidin-2-ylidene)-N-methyl-N-(2-methylphenyl)-acetamide; mp 114°–115° C. (diisopropyl ether)
- (n) (Z)-(3-methyl-4-oxothiazolidin-2-ylidene)-N-methyl-N-(3-methylphenyl)-acetamide; mp 117°–118° C. (diisopropyl ether)
- (o) (Z)-(3-methyl-4-oxothiazolidin-2-ylidene)-N-methyl-N-(2,6-dimethylphenyl)-acetamide; mp 153°–154° C. (diisopropyl ether)
- (p) (Z)-(3-ethyl-4-oxothiazolidin-2-ylidene)-N-(2,6-dimethylphenyl)-acetamide; mp 282.3° C. (decomp.) (propan-2-ol)
- (q) (Z)-(3-allyl-4-oxothiazolidin-2-ylidene)-N-(2,6-dimethylphenyl)-acetamide; mp 250.5° C. (decomp.) (propan-2-ol/water)
- (r) (Z)-(3-benzyl-4-oxothiazolidin-2-ylidene)-N-(2,6-dimethylphenyl)-acetamide; mp 182°–184° C. (toluene)
- (s) 3-methyl-2-[(3-methyl-4-oxothiazolidin-2-yliden)acetylamino]-benzoic acid ethyl ester; mp 167°–168° C. (THF/Petrolether)
- (t) (Z)-N-(methoxy-6-methyl-phenyl)-(3-methyl-4-oxothiazolidin-2-yliden)-acetamide; mp 158°–160° C. (isopropanol)
- (u) (Z)-N-(2-methylthio-phenyl)-3-methyl-4-oxothiazolidin-2-yliden)acetamide; mp 177°–178° C. (toluol)
- (v) (Z)-3-methyl-4-oxothiazolidin-2-ylidene)-N-3,4,5-trimethoxyphenyl)acetamide; mp 224°–225° C. (isopropanol)
- (w) (Z)-N-(2-methyl-6-nitro-phenyl)-(3-methyl-4-oxothiazolidin-2-yliden)acetamide; mp 218°–219° C. (toluol/dimethylketone)
- (x) (Z)-N-(2-diethylaminoethyl)-N-(2,6-xylyl)-(3-methyl-4-oxothiazolidin-2-yliden)-acetamide; HBr; mp 261.5° C. (ethanol)
- (y) Z-(3-methyl-4-oxothiazolidin-2-yliden)acetanilid.
- (z) Z-N-(4-chloro-2-nitrophenyl)-(3-methyl-4-oxothiazolidin-2-yliden)acetamide; mp 264°–265° C. (DMF/H$_2$O)
- (aa) 2-hydroxy-4-[(3-methyl-4-oxothiazolidin-2-yliden)acetylamino]-benzoic acid ethyl ester; mp 236°–237° C. (DMF/H$_2$O)
- (bb) (Z)-N-(3-diethylaminopropyl)-N-2,6-xylyl)-(3-methyl-4-oxothiazolidin-2-yliden)acetamide; HCl. mp 222°–223° C. (isopropanol)
- (cc) (Z)-N-(2-dimethylaminoethyl)-N-(2,6-xylyl)-(3-methyl-4-oxothiazolidin-2-yliden)acetamide; HCl. Mp 268.8° C. (ethanol)
- (dd) (Z)-N-(3-dimethylaminopropyl)-N-(2,6xylyl)-(3-methyl-4-oxothiazolidin-2-yliden)acetamide; HBr. Mp 253.6° C. (ethanol)
- (ee) (Z)-3-methyl-2-(3-methyl-4-oxothiazolidin-2-yliden)acetylamino-benzoic acid; mp 187° C. (dichloromethane)
- (ff) (Z)-(4-oxo-3-phenyl-thiazolidin-2-yliden)-N-(2,6-xylyl)acetamide; mp 228.3° C. (ethanol)
- (gg) (Z)-N-(2-chloro-6-methylphenyl)-(4-oxo-3-phenyl-thiazolidin-2-yliden)acetamide; mp 213°–214° C. (ethanol)
- (hh) (Z)-(3,5-dimethyl-4-oxothiazolidin-2-ylidene)-N-(2,6-xylyl)-acetamide; mp 220°–222° C. (ethanol).

PHARMACOLOGICAL COMPARATIVE EXPERIMENTS

Methodology

General

In the case of all substances, there was used in the cramp test as vehicle 0.8% Methocel mucilage. The premedication time amounted to 30 minutes, insofar as nothing else is stated, and the administration took place i.g. in 20 ml/kg body weight.

Experimental animals were male mice (NMRI) with a body weight of 18 to 24 g., which were kept under controlled conditions. Twenty-four hours (if not stated otherwise) before commencement of the experiment, the feed was withdrawn but, up to the commencement of the experiment, the drinking water was left.

In the case of the audiogenic cramps, DBA/2j mice of male sex were used in a weight of 5–10 g which, on the day before the experiment, were removed and not fasted.

Per dosage, in each case ten animals were subjected to the test.

As positive standard, there were used phenytoin, valproate, GABA and baclofen.

Test Models

1. Isoniazide cramp—As convulsive, there was used isonicotinic acid hydrazide (isoniazide) in a dosage of 250 mg/kg s.c., whereby the observation time amounted to 90 minutes.
2. Strychnine cramp—As convulsive, there was used strychnine nitric cryst in a dosage of 1.1 mg/kg s.c., whereby the observation time amount to 20 minutes p.a.
3. Electroshock—For the electroshock, there was used the HSE-shock stimulation apparatus Type 207. For the transmission of the current impact, electrodes in the form of ear clips were fixed to the ears of the mouse. The period of the shock amounted to 0.3 s., the current strength to 35 mA (voltage self-regulating). As positive standard, there was used phenytoin sodium in a dosage of 50 mg/kg i.g. or s.c. The period of observation was fixed at five minutes.
4. Pentetrazole cramp—As convulsive, there were administered 140 mg/kg pentetrazole s.c. The observation time amounted to 20 minutes.
5. Picrotoxin cramp—Picrotoxin was administered in a dosage of 15 mg/kg s.c. The animals were observed for 20 minutes.
6. Bicuculline cramp—Cramp agent was bicuculline purum. The dosage amounted to 3.0 mg/kg s.c. The observation time amount to 20 minutes.
7. Semicarbazide cramp—Semicarbazide hydrochloride was used as cramp agent in a dosage of 1000 mg/kg s.c. The observation time amounted in each case to 90 minutes p.a.
8. 3-Mercaptopropionic acid—3-Mercaptopropionic acid was diluted with physiological NaCl solution, adjusted with 6 mol/l NaOH to PH 7 and brought with NaCl solution to the end volume (10 ml/kg). The observation time amounted to 30 minutes.
9. Audiogenic cramps—The animals were acoustically irradiated for 30 seconds with a 10.9 KHz-sound of 110 dBA. The observation time amount to one minute.

TABLE I

| | Comparative Investigations of the Anticonvulsive Action in Cramp Models 1-9 $ED_{50}$ (mg/kg i.g., mouse ♂) | | | | | | | | |
|---|---|---|---|---|---|---|---|---|---|
| | Electro-shock | Pente-trazole cramp | Semi-carbazide cramp | Picrotoxin cramp | Strychnine cramp | 3-MPA cramp | isoni-azide cramp | Bicucul-line cramp | audio-genic cramp |
| Substance Example Number | | | | | | | | | |
| 2 (a) | 13.6 | 19.85 | 14.06 | 11.30 | 14.88 | 8.7 | 5.32 | 2.68 | 2.9 |
| 2 (i) | 6.47 | 1.90 | 1.59 | 2.34 | 5.09 | 1.29 | 1.24 | 0.9 | 3.0 |
| 2 (j) | 4.03 | 1.80 | 3.41 | 1.52 | 5.68 | 1.73 | 5.0 | 0.8 | 2.0 |
| comparative substances | | | | | | | | | |
| phenytoin | 50 (ED 100) 12.5 (i.v.) | 50 (ED 100) | 50 (ED 90) | 200 | inactive | — | 38 | 12.5 | 2.3 |
| valproate | 200 (ED 40) | 250 (ca.) | 100 | inactive | inactive | 154 | 135 | — | — |
| GABA | inactive | 500 | 60 | inactive | inactive | — | — | — | — |
| baclofen* | 20 | 100 | 4 | 30 | 8.5 | 20 | 2.0 | 20 | 5 |

*Side effects in all models.

Acute Toxicity and Therapeutic Index

The determination of the acute toxicity was carried out on male mice (NMRI) with a body weight of 18-23 g. All experimental animals were fasted for 20 hours before commencement of the experiment. Water was available ad libitum. To each dosage group there belonged four animals. The dosage sequence was logarithmic. The test substances were administered intragastrally as suspension in 0.88% Methocel. The volume of administration amounted to 20 ml/kg. The animals were observed for a total of seven days.

TABLE II

| Substance Example No. | $LD_{50}$ mg/kg i.g. (mouse ♂) | Therapeutic Index $LD_{50}/ED_{50}$* |
|---|---|---|
| 2 (a) | 1980 | 99.8-738.8 |
| 2 (i) | >1600 | >243.3-1777.8 |
| 2 (j) | 1600 | 281.6-2000 |
| valproate | 2000 | 8-14.8 |
| GABA | >5000 | >10-80 |
| phenytoin | 490 | 2.5-213 |
| baclofen* | 200 | 2-100 |

*In each case calculated for the largest and smallest $ED_{50}$ value.

From Tables I and II there follows the superior activity spectrum of the compounds, on the the one hand, (Table I) and the extraordinarily favorable relative safety on the basis of the therapeutic quotients (Table II), on the other hand.

We claim:
1. A compound, of the formula

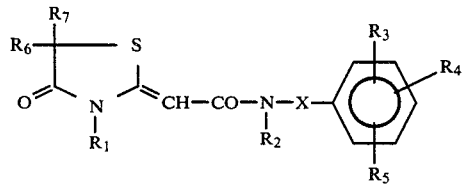

in which $R_1$ signifies a hydrogen atom, a saturated or unsaturated alkyl radical with one to three carbon atoms, a phenyl or benzyl radical, $R_2$ signifies a hydrogen atoms, or a methyl or ethyl group, or a dialkylaminoalkyl radical with up to seven carbon atoms, X signifies a valency bond or a straight-chained or branched alkylene group with one to three carbon atoms and $R_3$, $R_4$, and $R_5$, which can be the same or different, signify a hydrogen atom, a methyl, ethyl, methoxy, ethoxy, methylthio or ethylthio group, whereby two neighboring radicals can together also form a methylenedioxy group, a fluorine, chlorine, bromine, iodine atom, or a hydroxy group or a nitro group or a carboxyl radical or a lower alkoxycarbonyl radical with up to five carbon atoms and $R_6$ and $R_7$ which can be the same or different signify a hydrogen atom or a methyl or ethyl group, or a pharmaceutically acceptable acid addition salt thereof.

2. A compound according to claim 1, in which $R_1$ signifies a hydrogen atom, a methyl, ethyl, allyl or benzyl radical, $R_2$ signifies a hydrogen atom or a methyl radical, X signifies a valency bond or an ethylidene group and $R_3$, $R_4$ and $R_5$, which can be the same or different, signify a hydrogen atom, a methyl radical or a chlorine or bromine atom and $R_6$ and $R_7$ signify a hydrogen atom.

3. (Z)-(3-Methyl-4-oxothiazolidin-2-ylidene)-N-(2,6-dimethylphenyl)-acetamide.

4. (Z)-(3-Methyl-4-oxothiazolidin-2-ylidene)-N-(2-chloro-6-methylphenyl)-acetamide.

5. (Z)-(3-Methyl-4-oxothiazolidin-2-ylidene)-N-(2,6-dichlorophenyl)-acetamide.

6. A pharmaceutical composition for treating epilepsy comprising an effective amount of a compound according to claim 1 in admixture with a pharmaceutically acceptable carrier.

7. A method for treating epilepsy which comprises administering to a subject suffering therefrom an effective amount of a composition according to claim 6.

* * * * *